United States Patent
Kumar (10) Patent No.: US 10,124,177 B2
(45) Date of Patent: Nov. 13, 2018

(54) SYSTEMS AND METHODS FOR PROGRAMMING IMPLANTABLE DEVICES

(71) Applicant: PACESETTER, INC., Sylmar, CA (US)

(72) Inventor: Prasanna Kumar, Frisco, TX (US)

(73) Assignee: PACESETTER, INC., Sylmar, CA (US)

( * ) Notice: Subject to any disclaimer, the term of this patent is extended or adjusted under 35 U.S.C. 154(b) by 355 days.

(21) Appl. No.: 14/931,482

(22) Filed: Nov. 3, 2015

(65) Prior Publication Data
US 2017/0120062 A1    May 4, 2017

(51) Int. Cl.
*A61N 1/08*    (2006.01)
*A61N 1/372*   (2006.01)
*G05B 19/042*  (2006.01)
*A61N 1/36*    (2006.01)

(52) U.S. Cl.
CPC ..... *A61N 1/37282* (2013.01); *A61N 1/36132* (2013.01); *A61N 1/36146* (2013.01); *A61N 1/37241* (2013.01); *A61N 1/37247* (2013.01); *G05B 19/0426* (2013.01); *G05B 2219/23039* (2013.01)

(58) Field of Classification Search
CPC .. A61N 1/08; A61N 1/37252; A61N 1/36132; A61N 1/37282; G06F 19/00; A61B 5/0031
See application file for complete search history.

(56) References Cited

U.S. PATENT DOCUMENTS

| 7,212,110 | B1 | 5/2007 | Martin et al. |
| 7,228,179 | B2 | 6/2007 | Campen et al. |
| 7,571,007 | B2 | 8/2009 | Erickson et al. |
| 7,742,821 | B1 | 6/2010 | Vamos et al. |
| 2005/0137644 | A1* | 6/2005 | Boveja .............. A61N 1/36053 607/40 |
| 2006/0170486 | A1 | 8/2006 | Tranchina et al. |
| 2006/0195342 | A1* | 8/2006 | Khan .................... G06Q 10/10 705/3 |
| 2008/0097554 | A1* | 4/2008 | Payne ................. A61N 1/3787 607/61 |

(Continued)

FOREIGN PATENT DOCUMENTS

WO    0193953  A1    12/2001

*Primary Examiner* — Phuc Dang (57) ABSTRACT

The present disclosure provides systems and methods for programming an implanted device when a patient is remote from a clinician. A system includes a patient programmer configured to be operated by the patient, a clinician programmer configured to be operated by the clinician, and a remote diagnostic server configured to facilitate secure communication between the patient programmer and the clinician programmer, wherein the remote diagnostic server is configured to initiate a secure programming session between the patient programmer and the clinician programmer, receive a proposed stimulation program from the clinician programmer, transmit the proposed stimulation program to the patient programmer, receive an indication from the patient programmer that the patient has accepted the proposed stimulation program, and transmit an alert to the clinician programmer, the alert indicating that the patient has accepted the proposed stimulation program.

17 Claims, 5 Drawing Sheets

(56) References Cited

U.S. PATENT DOCUMENTS

| | | | |
|---|---|---|---|
| 2010/0222845 A1* | 9/2010 | Goetz | A61N 1/37252 |
| | | | 607/59 |
| 2010/0223020 A1* | 9/2010 | Goetz | A61B 5/0031 |
| | | | 702/104 |
| 2012/0096381 A1* | 4/2012 | Milne | A61M 16/0051 |
| | | | 715/771 |
| 2012/0137249 A1* | 5/2012 | Milne | A61M 16/0051 |
| | | | 715/808 |
| 2014/0275928 A1* | 9/2014 | Acquista | A61B 5/04085 |
| | | | 600/382 |
| 2016/0228693 A1* | 8/2016 | Vardiman | A61N 1/0534 |

* cited by examiner

SYSTEMS AND METHODS FOR PROGRAMMING IMPLANTABLE DEVICES

FIELD OF THE DISCLOSURE

The present disclosure relates generally to neurostimulation systems, and more particularly to programming neurostimulation systems when a patient is located remotely from a clinician.

BACKGROUND ART

Neuromodulation systems provide pain relief for patients by applying electrical stimulation. For example, spinal chronic pain patients may be implanted with spinal cord stimulation (SCS) devices, and movement disorder (e.g., Parkinson's) patients may be implanted with deep brain stimulation (DBS) devices.

In known neuromodulation systems, patients may be provided with external programmer devices that allow them to modify certain stimulation parameters within a range defined by their clinician. To receive reprogramming, however, patients must travel to visit the clinician in person multiple times a year (e.g., to provide feedback and to discuss therapy with the clinician). Commuting to visit the clinician is generally undesirable to patients, as it costs time and money, and results in added stress.

BRIEF SUMMARY OF THE DISCLOSURE

In one embodiment, the present disclosure is directed to a system for programming an implanted device when a patient is remote from a clinician. The system includes a patient programmer configured to be operated by the patient, a clinician programmer configured to be operated by the clinician, and a remote diagnostic server configured to facilitate secure communication between the patient programmer and the clinician programmer, wherein the remote diagnostic server is configured to initiate a secure programming session between the patient programmer and the clinician programmer, receive a proposed stimulation program from the clinician programmer, transmit the proposed stimulation program to the patient programmer, receive an indication from the patient programmer that the patient has accepted the proposed stimulation program, and transmit an alert to the clinician programmer, the alert indicating that the patient has accepted the proposed stimulation program.

In another embodiment, the present disclosure is directed to a remote diagnostic server for use in programming an implanted device when a patient is remote from a clinician. The remote diagnostic server includes a memory device, and a processor communicatively coupled to the memory device, the processor configured to initiate a secure programming session between a patient programmer operated by the patient and a clinician programmer operated by the clinician, receive a proposed stimulation program from the clinician programmer, transmit the proposed stimulation program to the patient programmer, receive an indication from the patient programmer that the patient has accepted the proposed stimulation program, and transmit an alert to the clinician programmer, the alert indicating that the patient has accepted the proposed stimulation program.

In another embodiment, the present disclosure is directed to a method for programming an implanted device when a patient is remote from a clinician. The method includes initiating, using a remote diagnostic server, a secure programming session between a patient programmer operated by the patient and a clinician programmer operated by the clinician, receiving, at the remote diagnostic server, a proposed stimulation program from the clinician programmer, transmitting, from the remote diagnostic server, the proposed stimulation program to the patient programmer, receiving, at the remote diagnostic server, an indication from the patient programmer that the patient has accepted the proposed stimulation program, and transmitting, from the remote diagnostic server, an alert to the clinician programmer, the alert indicating that the patient has accepted the proposed stimulation program.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for programming an implanted device when a patient is remote from a clinician. A remote diagnostic server initiates a secure programming session between a patient programmer operated by the patient and a clinician programmer operated by the clinician. The clinician programmer transmits a proposed stimulation program to the remote diagnostic server, which in turn transmits the proposed stimulation program to the patient programmer. If the patient approves of the proposed stimulation program, the patient uses the patient program to indicate approval and to program the implanted device accordingly.

Neurostimulation systems are devices that generate electrical pulses and deliver the pulses to nerve tissue of a patient to treat a variety of disorders. One category of neurostimulation systems is deep brain stimulation (DBS). In DBS, electrical pulses are delivered to parts of a subject's brain, for example, for the treatment of movement and effective disorders such as PD and essential tremor. Another category of neurostimulation systems is spinal cord stimulation (SCS), in which electrical stimulation is applied to the spinal cord of a patient.

Neurostimulation systems generally include a pulse generator and one or more leads. A stimulation lead includes a lead body of insulative material that encloses wire conductors. The distal end of the stimulation lead includes multiple electrodes, or contacts, that are electrically coupled to the wire conductors. The proximal end of the lead body includes multiple terminals (also electrically coupled to the wire conductors) that are adapted to receive electrical pulses. In DBS systems, the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted within a subcutaneous pocket created during the implantation procedure.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Figure 1:
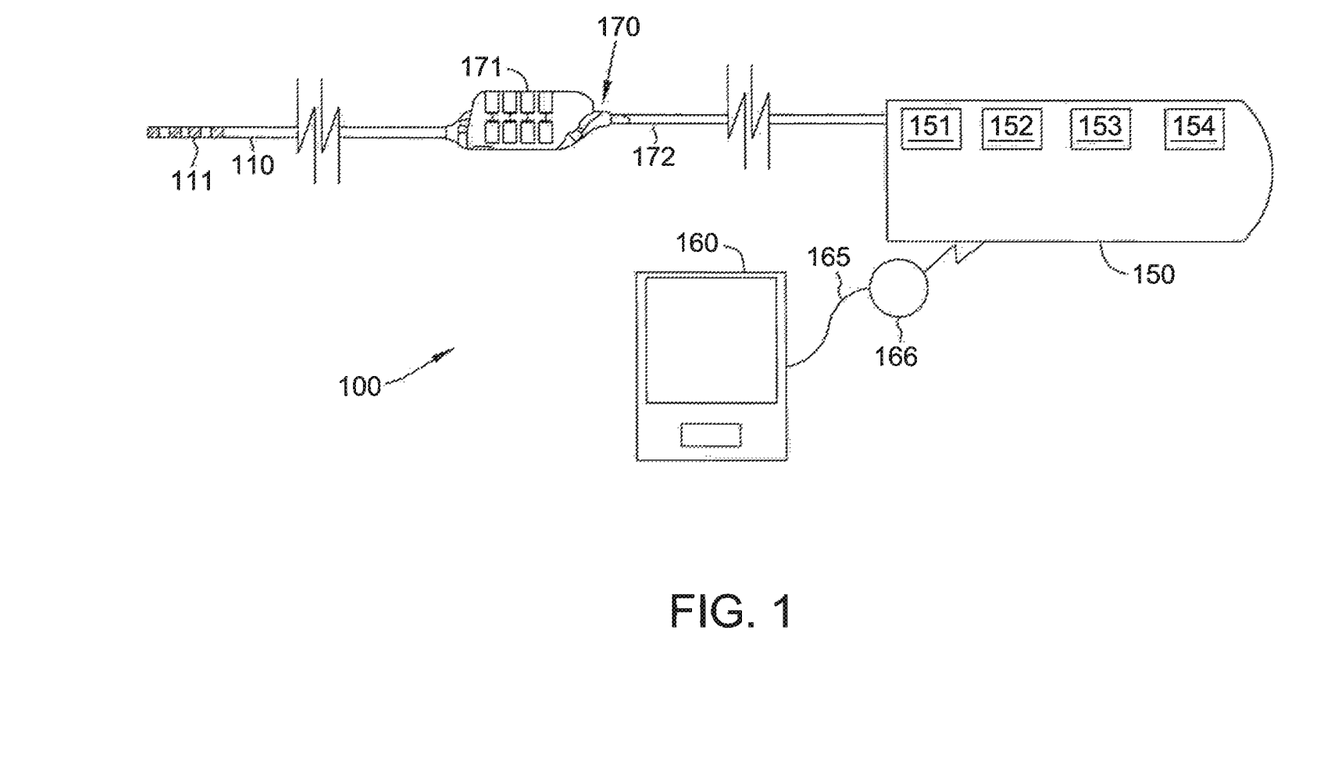
FIG. 1 is a schematic view of one embodiment of a stimulation system.

Referring now to the drawings and in particular to FIG. 1, a stimulation system is indicated generally at 100. Stimulation system 100 generates electrical pulses for application to tissue of a patient, or subject, according to one embodiment. System 100 includes an implantable pulse generator 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of implantable pulse generator 150 for execution by the microcontroller or processor to control the various components of the device.

Implantable pulse generator 150 may comprise one or more attached extension components 170 or be connected to one or more separate extension components 170. Alternatively, one or more stimulation leads 110 may be connected directly to implantable pulse generator 150. Within implantable pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from implantable pulse generator 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within implantable pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 150. Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of implantable pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

External controller device 160 is also a device that permits the operations of implantable pulse generator 150 to be controlled by user after implantable pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with implantable pulse generator 150.

Controller device 160 preferably provides one or more user interfaces to allow the user to operate implantable pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from St. Jude Medical, Inc. (Plano, Tex.).

In the system and methods described herein, a mobile computing device functions as a programmer, such as controller device 160 (shown in FIG. 1). By facilitating communication between patients and clinicians, an implanted device (e.g., an implantable pulse generator (IPG) for a deep brain stimulation (DBS) system or a spinal cord stimulation (SCS) system) may be programmed when the patient is located remotely from the clinician. Although the systems and methods described herein are explained in the context of neurostimulation systems, those of skill in the art will appreciate that the systems and methods described herein may also be used to remotely program cardiac stimulation systems in some embodiments.

Figure 2:
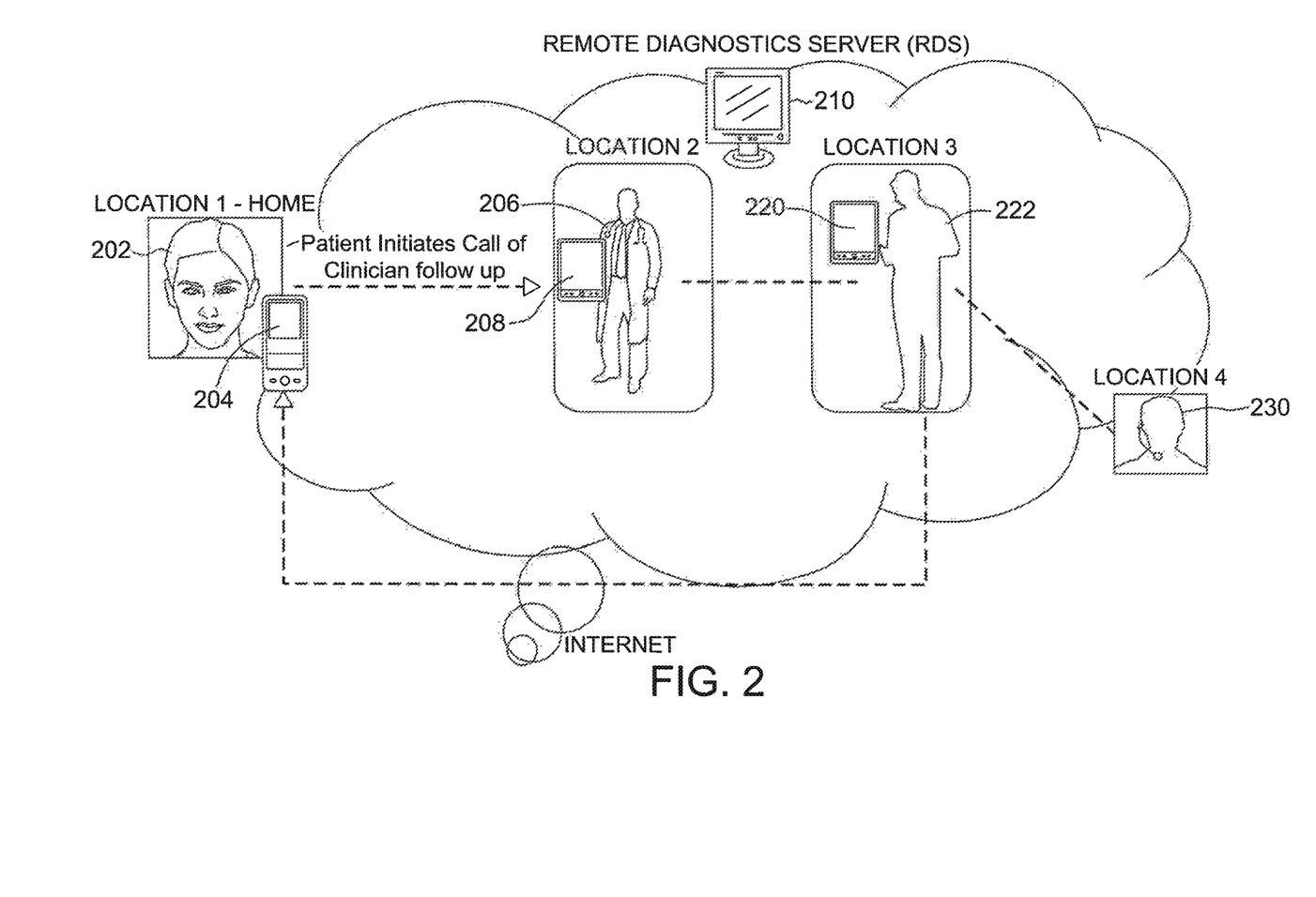
FIG. 2 is a schematic diagram of one embodiment of a system that may be used to program the stimulation system shown in FIG. 1.

FIG. 2 is a schematic diagram of one embodiment of a system 200 for programming an implantable device. In this embodiment, a patient 202 uses a patient programmer (PP) 204 and a clinician 206 uses a clinician programmer (CP) 208 to facilitate programming the implantable device, as described herein. PP 204 may be, for example, a mobile phone and CP 208 may be, for example, a tablet computing device. Alternatively, PP 204 and CP 208 may be any suitable computing devices that enable system 200 to function as described herein. PP 204 and CP 208 are capable of providing fully integrated voice, video, and programming capabilities remotely between patient 202 and clinician 206, as described herein. Further, system 200 is implemented using software applications operating on PP 204 and CP 208.

As noted above, in this embodiment, system 200 is used to program an IPG in a neuromodulation system, such as a DBS system or a SCS system. Notably, the systems and methods described herein allow chronic pain patients to perform device programming on a daily basis, and allow patients to switch between multiple predetermined stimulation programs generated by clinicians or other parties. In this embodiment, the adjustable stimulation parameters include amplitude (e.g., for patient comfort and perception levels), frequency range, pulse width range, and electrode configuration. Alternatively, system 200 may allow for adjustment of any suitable stimulation parameters. The parameters may be adjustable, for example, in predetermined increments (i.e., step sizes).

The implanted device (e.g., the IPG in the DBS or SCS system) communicates with PP 204. In this embodiment, PP 204 and CP 208 both have Wi-Fi capability. Further, using CP 208, clinician 206 is able to generate new stimulation programs and transmit the generated stimulation programs to PP 204. PP 204 and CP 208 communicate with one another via a remote diagnostic server (RDS) 210. RDS 210 also stores data for communication between PP 204 and CP 208 for future use.

In system 200, PP 204 and CP 208 communicate with one other over the Internet using RDS 210. Audio and video communications between PP 204 and CP 208 may also be performed using, for example, a cellular network or a video conferencing service.

In this embodiment, RDS 210 uses software hooks (e.g., application programming interfaces (APIs)) to connect with software applications operating on PP 204 and CP 208. That is, APIs bridge communications from RDS 210 between PP 204 and CP 208. Through the software applications, in a native or local mode, PP 204 and CP 208 both provide stimulation programming capabilities for patients and clinicians, respectively. In a remote programming mode, the APIs provide remote connectivity. Notably, PP 204 and CP 208 can communicate over the Internet using a Wi-Fi network, and do not require customized telemetry devices, or plain old telephone service (POTS), 3G, or 4G connections to operate.

To initiate operation of system 200, a connection is initiated between PP 204 and CP 208 by making a call between devices (e.g., using a video conferencing application or a cellular network). Once the initial connection between PP 204 and CP 208 is established, RDS 210 uses APIs to establish a secure connection by invoking the remote programming mode, as described below. Clinician 206 may also request data from the implanted device via RDS 210.

In this embodiment, system 200 further includes a representative programmer (RP) 220 operated by a representative 222. Representative 222 may by employed, for example, for the company that provides the implanted device being programmed. In addition to CP 208, RP 220 may also be used to program the implanted device. In some embodiments, system 200 does not include RP 220.

To create a new stimulation program, using CP 208 or RP 220, the user (i.e., clinician 206 or representative 222) specifies a plurality of initial parameters via a software application running on CP 208 or RP 220. In this embodiment, the user specifies i) an electrode configuration, ii) an amplitude, iii) a frequency, and iv) a pulse width for the stimulation. Alternatively, the user may specify any suitable number and type of stimulation parameters. For each initial parameter, patient 202 is notified of the user selection, and is given the opportunity to accept or decline the selected initial parameter. Once patient 202 accepts an initial parameter value, that value is written into the implanted device from PP 204.

After the initial parameters are set, patient 202 may provide feedback to clinician 206 and/or representative 222 (e.g., via video or voice communication) to increase or decrease the parameters, as desired. For example, clinician 206 may increase a parameter (e.g., amplitude) and then ask patient 202 whether the increased parameter provides additional relief or less relief. If the increased parameter provides additional relief, clinician 206 may further increase the parameter. For each changed parameter value, a notification is displayed on PP 204 (e.g., via a pop up window) that allows patient 202 to accept or decline the parameter modification. In this embodiment, once patient 202 is satisfied with the stimulation program, patient 202 selects a "program accept" button.

The accepted stimulation program is stored in RDS 210 as part of the programming session, and is also saved in the implanted device such that the implanted device provides stimulation in accordance with the accepted stimulation program. If, at any time during operation of the implanted device, patient 202 finds the accepted stimulation program causes discomfort or does not provide sufficient pain relief, patient 202, using PP 204, can delete the accepted stimulation program from the implanted device, causing implanted device to operate in accordance with the previous stimulation program. Notably, in this embodiment, RDS 210 records data about the programming session, including, but not limited to, what stimulation parameters were changed and/or added, the date and time each modification was made, etc. Those of skill in the art will appreciate that the above steps may be used to create an initial stimulation program for the patient or to modify an existing stimulation program.

As shown in FIG. 2, patient 202, clinician 206 and representative 222 may all be located in different geographic locations (e.g., Location 1, Location 2, Location 3). However, RDS 210 enables communications between patient 202, clinician 206, and representative 222. Further, in some embodiments, a technical services party 230 in yet another separate geographic location provides technical support for system 200.

Figure 3A:
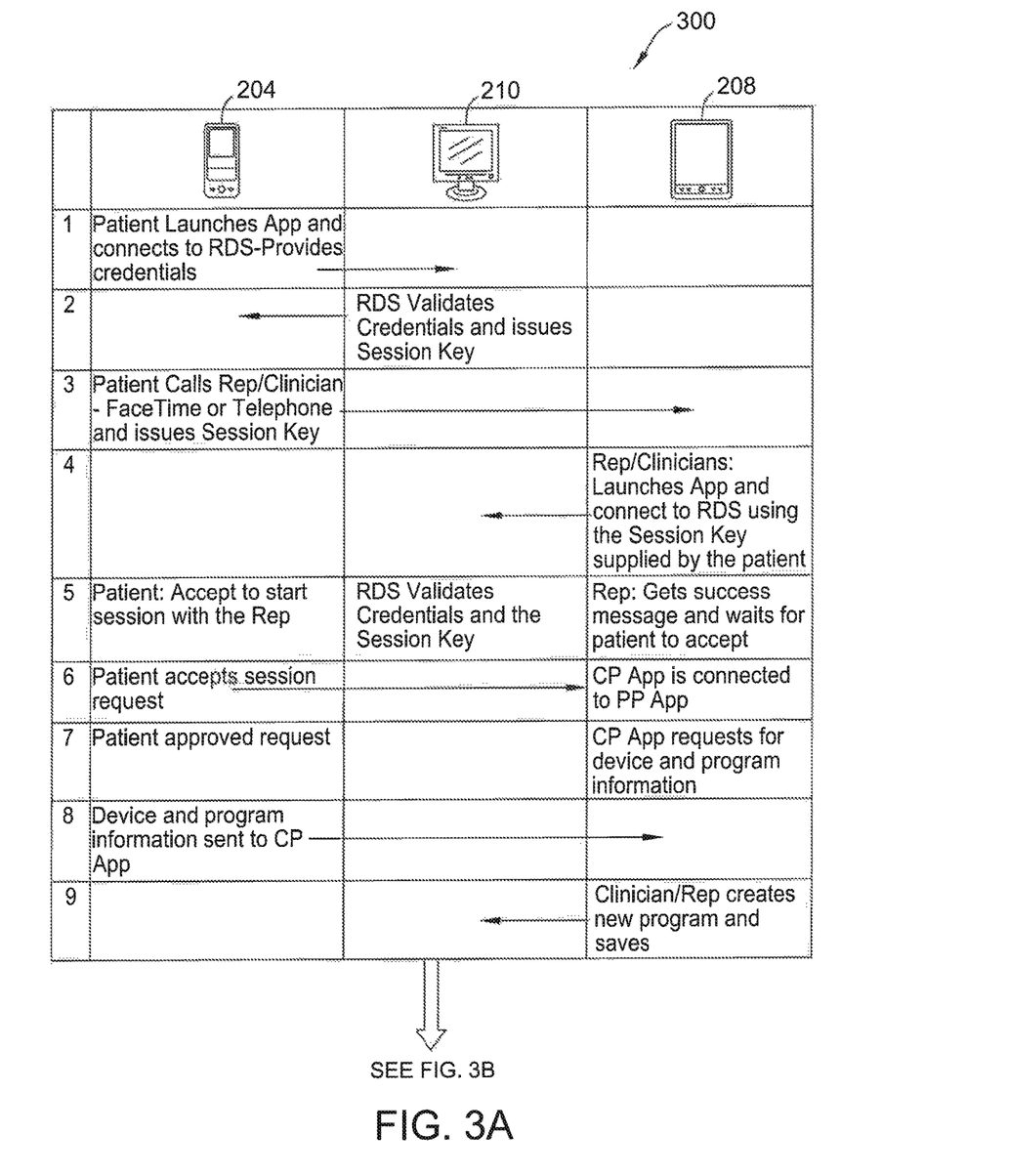
FIGS. 3A and 3B are a diagram of one embodiment of a programming session performed using the system shown in FIG. 2.
Figure 3B:
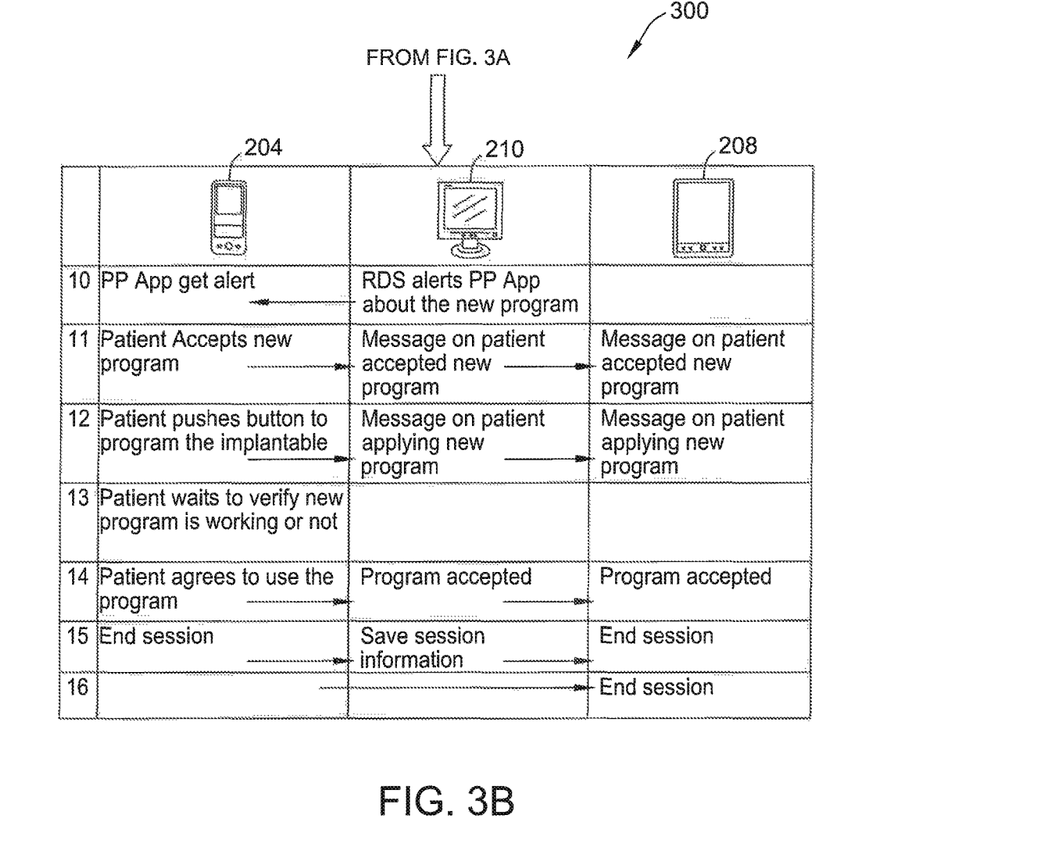

FIGS. 3A and 3B are a diagram of an example programming session 300 that may be performed using system 200 (shown in FIG. 2). Programming session 300 is implemented using PP 204, CP 208, RP 220, and RDS 210.

To initiate programming session 300, using PP 204, patient launches the remote programming application and connects to RDS 210 by providing appropriate credentials (e.g., username, password, etc.). RDS 210 validates the received credentials and issues a session key to PP 204. The session key is a unique identifier generated for each programming session. For security purposes, the session key is initially known by only patient 202, until patient 202 shares with other parties, as described herein.

Next, patient 202 contacts clinician 206 and/or representative 222 using regular telephone communications or a video conferencing application. During the call, patient 202 shares the unique session key with clinician 206 and representative 222. Clinician 206 and representative 222 then launch remote programming applications on CP 208 (and RP 220), and connect to RDS 210 using the session key provided by patient 202 and appropriate credentials (e.g., username, password, etc.).

RDS 210 validates the credentials and session key from CP 208 and RP 220. As a result, CP 208 and RP 220 receive a success message and wait for patient 202 to accept starting programming session 300. Once patient 202 accepts programming session 300 (via PP 204), RDS 210 initializes programming session 300 between CP 208 and PP 204.

To facilitate remote programming, clinician 206 uses CP 208 to request device and program information from the implantable device to be programmed. Patient 202 then authorizes (using PP 204) the device and program information to be transmitted from PP 204 to CP 208.

Clinician 206 and/or representative 222 generates a proposed stimulation program by creating a new stimulation program or adjusting the existing stimulation program, as described above. In response, RDS 210 generates and transmits an alert to PP 204 to notify patient 202 of the new or adjusted stimulation program.

Upon receiving the alert, if patient 202 approves of the new or adjusted stimulation program, patient 202 accepts the stimulation program using PP 204. In response to the acceptance, RDS 210 transmits a message to CP 208 to notify clinician 206. Patient 202 also uses PP 204 to program the implanted device with the approved stimulation program (and RDS 210 transmits a corresponding message to CP 208). Alternatively, upon patient 202 approving the stimulation program, the implanted device may be automatically programmed.

Upon receiving stimulation from the implanted device in accordance with approved stimulation program, patient 202 is able to determine whether the approved program provides sufficient pain relief. If patient 202 wants to continue using the approved program, patient indicates acceptance of the program using PP 204. In this embodiment, RDS 210 transmits a message to CP 208 indicating acceptance of the stimulation program by patient 202. In response to patient acceptance, RDS 210 saves information for programming session 300 (e.g., the date and time, the accepted stimulation program, etc.), and programming session 300 ends.

Figure 4:
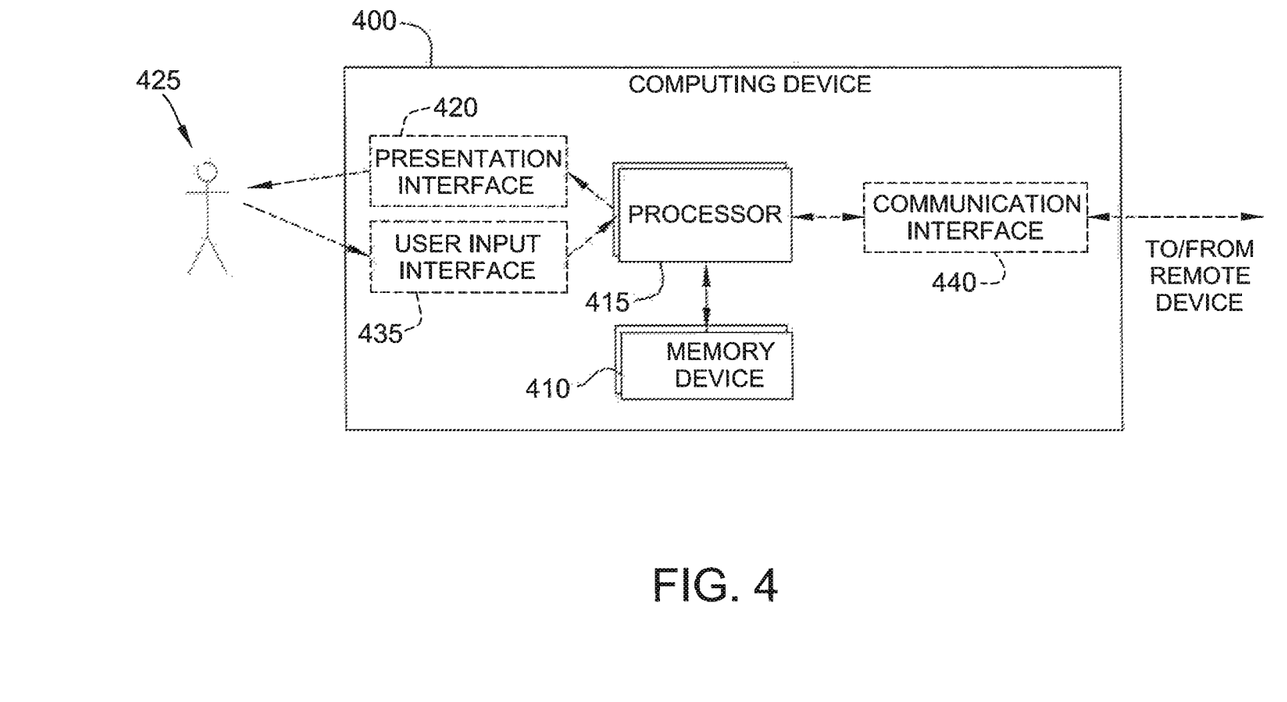
FIG. 4 is a block diagram of one embodiment of a computing device that may be used to implement the system shown in FIG. 2.

FIG. 4 is a block diagram of one embodiment of a computing device 400 that may be used to implement PP 204, CP 208, RP 220, and/or RDS 210. Computing device 400 includes at least one memory device 410 and a processor 415 that is coupled to memory device 410 for executing instructions. In some embodiments, executable instructions are stored in memory device 410. In this embodiment, computing device 400 is a specialized computing device that performs one or more operations described herein by programming processor 415. For example, processor 415 may be programmed by encoding an operation as one or more executable instructions and by providing the executable instructions in memory device 410.

Processor 415 may include one or more processing units (e.g., in a multi-core configuration). Further, processor 415 may be implemented using one or more heterogeneous processor systems in which a main processor is present with secondary processors on a single chip. In another illustrative example, processor 415 may be a symmetric multiprocessor system containing multiple processors of the same type. Further, processor 415 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), general purpose graphics processing unit (GPU), and any other circuit capable of executing the functions described herein.

In this embodiment, memory device 410 is one or more devices that enable information such as executable instructions and/or other data to be stored and retrieved. Memory device 410 may include one or more computer readable media, such as, without limitation, dynamic random access memory (DRAM), static random access memory (SRAM), a solid state disk, and/or a hard disk. Memory device 410 may be configured to store, without limitation, application source code, application object code, source code portions of interest, object code portions of interest, configuration data, execution events and/or any other type of data.

In this embodiment, computing device 400 includes a presentation interface 420 that is coupled to processor 415. Presentation interface 420 presents information to a user 425. For example, presentation interface 420 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 420 includes one or more display devices. Further, in some embodiments, presentation interface may not generate visual content, but may be limited to generating audible and/or computer-generated spoken-word content.

In this embodiment, computing device 400 includes a user input interface 435. User input interface 435 is coupled to processor 415 and receives input from user 425. User input interface 435 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 420 and user input interface 435.

Computing device 400, in this embodiment, includes a communication interface 440 coupled to processor 415. Communication interface 440 communicates with one or more remote devices. To communicate with remote devices, communication interface 440 may include, for example, a wired network adapter, a wireless network adapter, and/or a mobile telecommunications adapter.

In this embodiment, RDS 210 is an application server that includes a database to store session details, as described above. RDS 210 also pushes and pulls programming parameters between PP 204 and CP 208 as described above. Moreover, RDS 210 provides a secured connection between PP 204 and CP 208, and allows only registered patients 202, clinicians 206, and/or representatives 222 to communicate.

Further, in this embodiment, to implement the systems and methods described herein, PP 204 runs a regulatory-approved software application that enables communication between PP 204 and the implanted device. PP 204 also includes hardware capable of connecting to Wi-Fi or other interfaces to connect to the Internet. Notably, communications between the implanted device and PP 204, and between PP 204 and the Internet are secured and encrypted in this embodiment. The software application includes APIs that support remote programming of the implanted device, as described herein. Further, as described above, the software application on PP 204 initiates programming session 300 with RDS 210, and in response, RDS 210 generates a unique session key. The software application also reads data from the implanted device and sends that data to RDS 210 as part of programming session 300. The software application also facilitates receiving and displaying alerts on PP 204 upon creation of new or updated stimulation programs, and allows patient 202 to reject the new or updated stimulation programs if patient 202 desires to do so.

In this embodiment, CP 208 also runs a software application that is regulatory approved and able to communicate with RDS 210 (and optionally, the implanted device). CP 208 includes hardware capable of connecting to Wi-Fi or other interfaces to connect to the Internet Notably, communications between RDS 210 and CP 208 are secured and encrypted in this embodiment. The software application for CP 208 includes APIs that support remote programming of the implanted device, as described above. Further, as described above, the software application on CP 208 initiates programming session 300 with RDS 210 using the unique session key provided to clinician 206 by patient 202. CP 208 sends messages to RDS 210 to request patient device and programming information, as described above. Moreover, as described above, CP 208 allows clinician 206 to create new stimulation programs and adjust existing stimulation parameters, very similar to in-person in-clinic programming sessions. Once input, CP 208 transmits the new or adjusted stimulation program to RDS 210, and requests that RDS 210 transmit the stimulation program to PP 204.

In some embodiments, representative 222 uses RP 220 to create new stimulation programs or adjust existing stimulation programs. In such embodiments, before the new or adjusted stimulation program is sent to PP 204, clinician 206 must approve the new or adjusted stimulation program using CP 208. RDS 210 records this approval, along with other data from the session.

The systems and methods described herein facilitate remotely programming and implanted device, without requiring a patient to have an in person visit with their clinician. This saves travel time and costs, increases productivity, and reduces patient stress. The embodiments described herein also provide enhanced patient management for clinicians, and facilitate early detection of issues in stimulation systems (such as lead migration and elective replacement indicators (ERIs)).

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for programming an implanted device when a patient is remote from a clinician, the system comprising:
 a patient programmer configured to be operated by the patient;
 a clinician programmer configured to be operated by the clinician; and
 a remote diagnostic server configured to facilitate secure communication between the patient programmer and the clinician programmer, wherein the remote diagnostic server is configured to:
  initiate a secure programming session between the patient programmer and the clinician programmer;
  receive a proposed stimulation program from the clinician programmer;
  transmit the proposed stimulation program to the patient programmer;
  receive an indication from the patient programmer that the patient has accepted the proposed stimulation program; and
  transmit an alert to the clinician programmer, the alert indicating that the patient has accepted the proposed stimulation program;
  wherein to initiate a secure programming session, the remote diagnostic server is configured to:
   issue a unique session key to the patient programmer;

receive the unique session key from the clinician programmer; and initiate the secure programming session in response to receiving the unique session key from the clinician programmer.

2. The system of claim 1, further comprising a representative programmer, wherein the remote diagnostic server is further configured to include the representative programmer in the secure programming session.

3. The system of claim 1, wherein the patient programmer is configured to program the implanted device to operate in accordance with the proposed stimulation program.

4. The system of claim 3, wherein the implanted device is an implantable pulse generator of a deep brain stimulation system.

5. The system of claim 3, wherein the implanted device is an implantable pulse generator of a spinal cord stimulation system.

6. The system of claim 1, wherein the remote diagnostic server is configured to store data associated with the secure programming session; the stored data including the proposed stimulation program.

7. A remote diagnostic server for use in programming an implanted device when a patient is remote from a clinician, the remote diagnostic server comprising:

a memory device; and a processor communicatively coupled to the memory device, the processor configured to:

initiate a secure programming session between a patient programmer operated by the patient and a clinician programmer operated by the clinician;

receive a proposed stimulation program from the clinician programmer;

transmit the proposed stimulation program to the patient programmer;

receive an indication from the patient programmer that the patient has accepted the proposed stimulation program; and transmit an alert to the clinician programmer, the alert indicating that the patient has accepted the proposed stimulation program;

wherein to initiate a secure programming session, the processor is configured to:

issue a unique session key to the patient programmer;

receive the unique session key from the clinician programmer; and initiate the secure programming session in response to receiving the unique session key from the clinician programmer.

8. The remote diagnostic server of claim 7, wherein the processor is further configured to include a representative programmer in the secure programming session.

9. The remote diagnostic server of claim 7, wherein the processor is configured to receive a proposed stimulation program for an implantable pulse generator of a deep brain stimulation system.

10. The remote diagnostic server of claim 7, wherein the processor is configured to receive a proposed stimulation program for an implantable pulse generator of a spinal cord stimulation system.

11. The remote diagnostic server of claim 7, wherein the processor is configured to store data associated with the secure programming session in the memory device, the stored data including the proposed stimulation program.

12. A method for programming an implanted device when a patient is remote from a clinician, the method comprising:

initiating, using a remote diagnostic server, a secure programming session between a patient programmer operated by the patient and a clinician programmer operated by the clinician;

receiving, at the remote diagnostic server, a proposed stimulation program from the clinician programmer;

transmitting, from the remote diagnostic server, the proposed stimulation program to the patient programmer;

receiving, at the remote diagnostic server, an indication from the patient programmer that the patient has accepted the proposed stimulation program; and transmitting, from the remote diagnostic server, an alert to the clinician programmer, the alert indicating that the patient has accepted the proposed stimulation program;

wherein initiating a secure programming session comprises:

issuing a unique session key to the patient programmer;

receiving the unique session key from the clinician programmer; and initiating the secure programming session in response to receiving the unique session key from the clinician programmer.

13. The method of claim 12, further comprising including a representative programmer in the secure programming session.

14. The method of claim 12, further comprising programming, using the patient programmer, the implanted device to operate in accordance with the proposed stimulation program.

15. The method of claim 14, wherein programming the implanted device comprises programming an implantable pulse generator of a deep brain stimulation system.

16. The method of claim 14, wherein programming the implanted device comprises programming an implantable pulse generator of a spinal cord stimulation system.

17. The method of claim 12, further comprising storing data associated with the secure programming session, the stored data including the proposed stimulation program.

* * * * *